(12) United States Patent
O'Sullivan et al.

(10) Patent No.: US 12,721,961 B2
(45) **Date of Patent: *Sep. 1, 2026**

(54) POSITIVE EXHALATION PRESSURE DEVICE

(71) Applicant: Solopep Limited, County Clare (IE)

(72) Inventors: Kevin J. O'Sullivan, County Kerry (IE); Leonard W. O'Sullivan, County Clare (IE); Colum Dunne, County Tipperary (IE); Barry Linnane, Limerick (IE); Deirdre McGrath, Limerick (IE)

(73) Assignee: Solopep Limited, County Clare (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/598,626

(22) Filed: Mar. 7, 2024

(65) Prior Publication Data

US 2024/0285883 A1 Aug. 29, 2024

Related U.S. Application Data

(63) Continuation of application No. 17/021,577, filed on Sep. 15, 2020, now Pat. No. 11,951,253, which is a (Continued)

(30) Foreign Application Priority Data

Dec. 18, 2015 (EP) .................................... 15201412

(51) Int. Cl.
*A61M 16/00* (2006.01)
*A61M 15/00* (2006.01)
(Continued)

(52) U.S. Cl.
CPC .... *A61M 16/0006* (2014.02); *A61M 15/0018* (2014.02); *A61M 15/0098* (2014.02);
(Continued)

(58) Field of Classification Search
CPC .......... A61M 15/0018; A61M 15/0098; A61M 15/0008; A61M 16/0006; A61M 16/208
See application file for complete search history.

(56) References Cited

U.S. PATENT DOCUMENTS 4,841,964 A * 6/1989 Hurka .............. A61M 15/0028 128/203.23
5,018,517 A 5/1991 Liardet
(Continued)

FOREIGN PATENT DOCUMENTS

| | | | |
|---|---|---|---|
| EP | 0411714 | A1 | 2/1991 |
| EP | 1897597 | A2 | 3/2008 |
| WO | WO 9624407 | A1 | 8/1996 |

OTHER PUBLICATIONS

Extended Search Report for European Application No. 15201412.2 dated Mar. 8, 2016 (8 pages).

*Primary Examiner* — Chelsea E Stinson
*Assistant Examiner* — Anh Bui
(74) *Attorney, Agent, or Firm* — Bookoff McAndrews, PLLC

(57) ABSTRACT

A positive exhalation pressure device (1) is described. The device (1) comprises a housing (2) having an annular chamber (5), a chamber inlet (6) configured to permit air into the chamber, a chamber outlet (7) configured to permit air out of the chamber, and a mouthpiece (8) in fluid communication with the chamber inlet. A movable body such as a ball (3) is disposed in the housing within the annular chamber and configured to revolve around the annular chamber in response to flow of air through the chamber from the chamber inlet to the chamber outlet. The movable body is configured to at least partially block the chamber outlet as it revolves around the annular chamber causing cyclical fluctuations in airflow resistance.

20 Claims, 9 Drawing Sheets

Related U.S. Application Data continuation of application No. 15/383,657, filed on Dec. 19, 2016, now Pat. No. 10,806,876.

(51) Int. Cl.
*A61M 16/08* (2006.01)
*A61M 16/16* (2006.01)
*A61M 16/20* (2006.01)

(52) U.S. Cl.
CPC ..... *A61M 16/0866* (2014.02); *A61M 15/0008* (2014.02); *A61M 16/161* (2014.02); *A61M 16/208* (2013.01); *A61M 2205/0205* (2013.01); *A61M 2205/33* (2013.01); *A61M 2205/502* (2013.01); *A61M 2205/581* (2013.01); *A61M 2205/582* (2013.01); *A61M 2205/59* (2013.01); *A61M 2206/20* (2013.01)

(56) References Cited

U.S. PATENT DOCUMENTS

| | | | | |
|---|---|---|---|---|
| 10,806,876 | B2 * | 10/2020 | O'Sullivan ....... | A61M 16/0006 |
| 2011/0232636 | A1 * | 9/2011 | Von Hollen ...... | A61M 15/0086 128/203.29 |
| 2014/0041657 | A1 * | 2/2014 | Meyer .................. | A61M 16/14 128/203.12 |
| 2015/0053209 | A1 | 2/2015 | Meyer et al. | |
| 2015/0360079 | A1 * | 12/2015 | Keller ............... | A61M 16/0006 482/13 |
| 2016/0367751 | A1 * | 12/2016 | Bazargan ............... | F04B 51/00 |

* cited by examiner

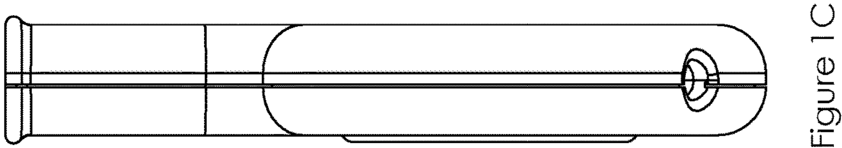
Figure 1C
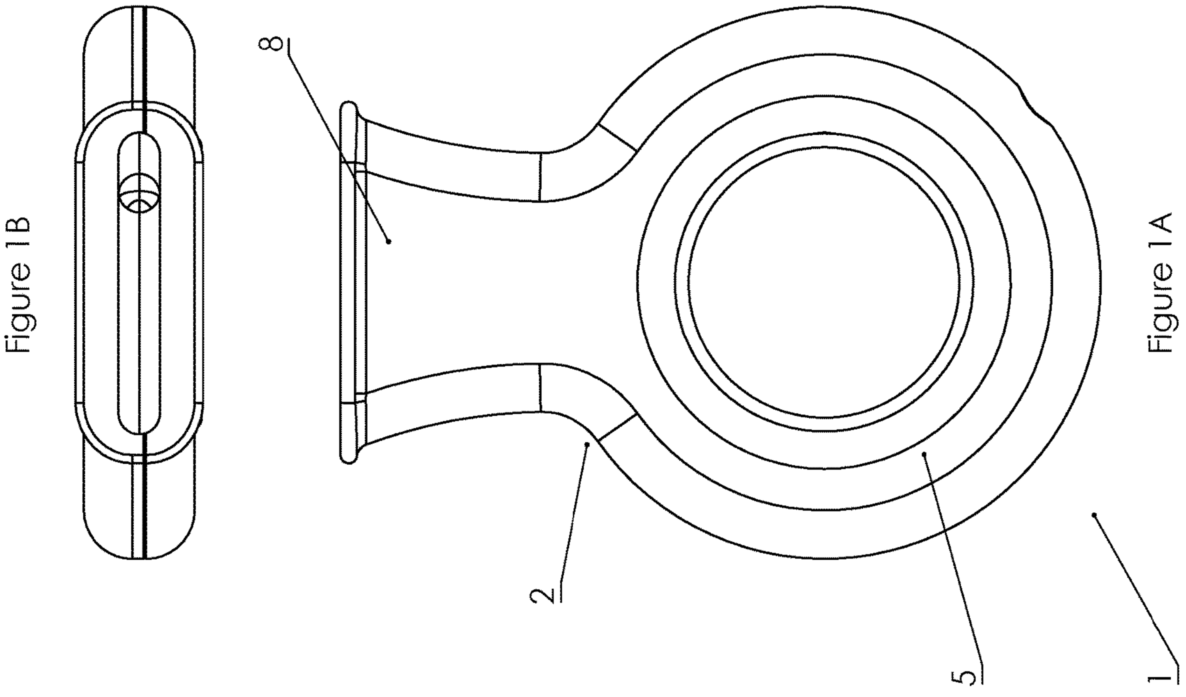
8
2
5
1
Figure 1B
Figure 1A 6
7
5
3

2B
11
9
7

10

2A
5
6
7

3

270

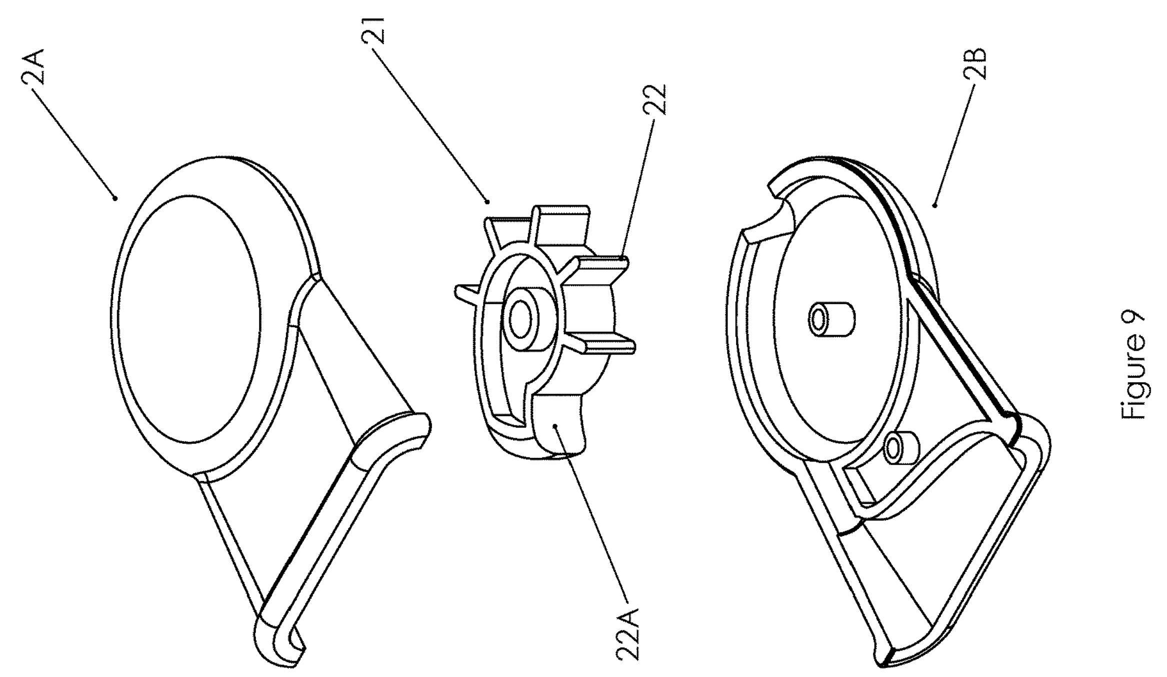
Figure 9
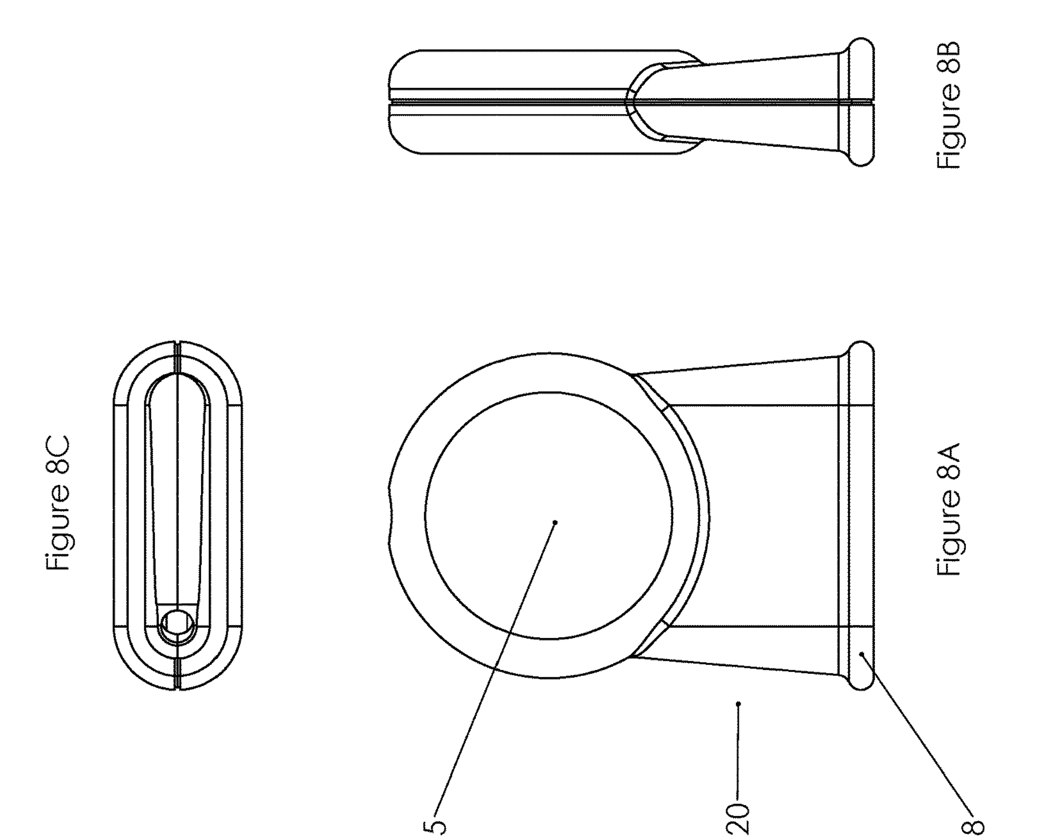
Figure 8C
Figure 8B
Figure 8A 21
8

21
22

22A
2A
5
7
23
9

2B
7
6
23

2A
31
2B 2B
2A
8

30

30
8

2B

2B 31
32A
31

32
2A
2B
7
8

6

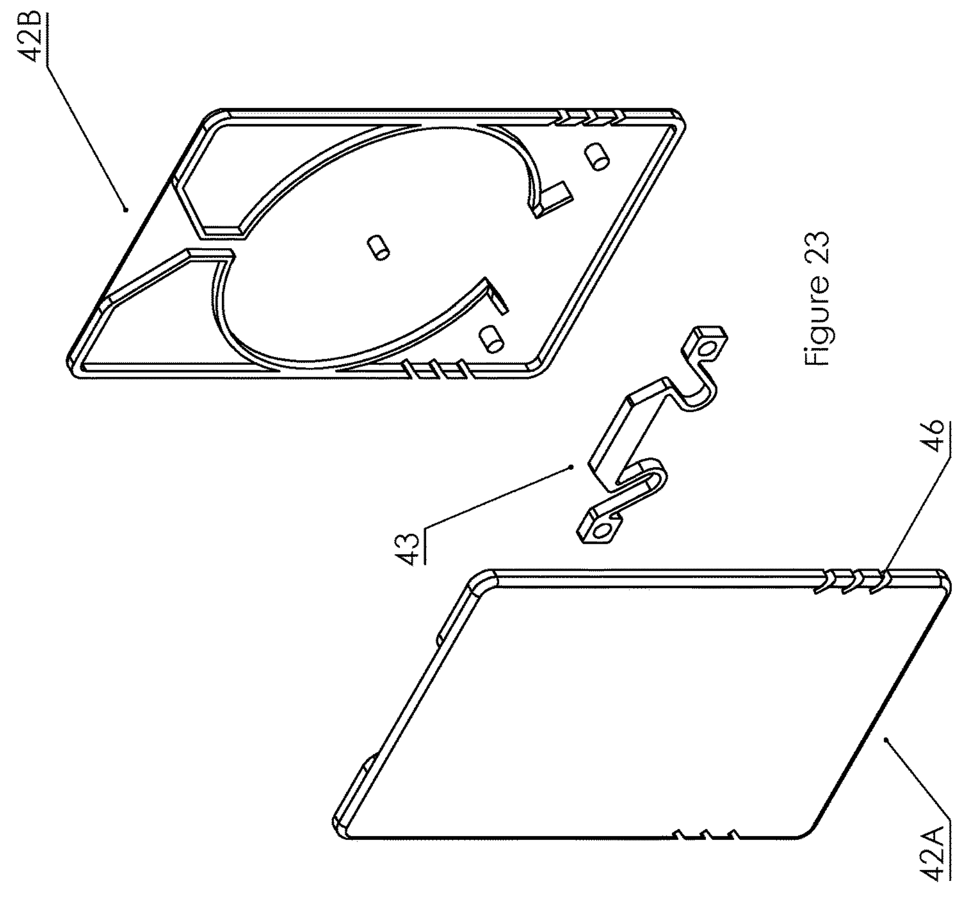
Figure 23
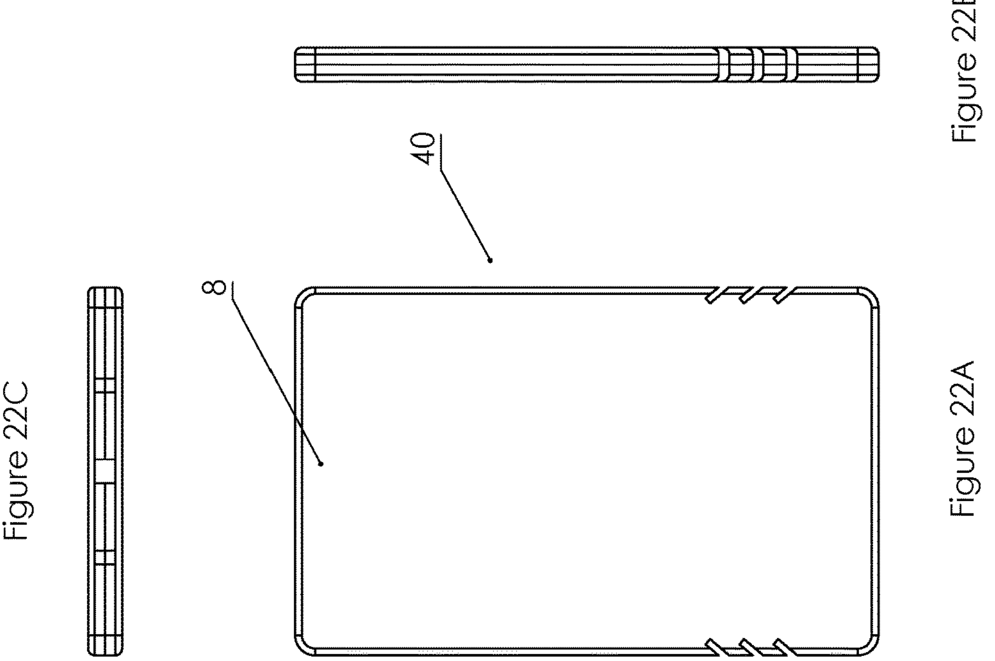
Figure 22A
Figure 22B
Figure 22C 8
6
44
45
45

43
44
45
45

2B
6
5
7

2A
8
6
5
7
46
46

POSITIVE EXHALATION PRESSURE DEVICE

CROSS REFERENCE TO RELATED APPLICATIONS

This application is a continuation of U.S. patent application Ser. No. 17/021,577, filed Sep. 15, 2020, which is a continuation of U.S. application Ser. No. 15/383,657, filed on Dec. 19, 2016, now U.S. Pat. No. 10,806,876, which claims priority to European Patent Application No. 15201412.2, filed on Dec. 18, 2015, each of which is incorporated herein by reference in its entirety.

BACKGROUND TO THE INVENTION

Positive Exhalation Pressure (PEP) therapy is used to mobilise secretions and treat atelectasis. Cough and other airway clearance techniques are essential components when the therapy is intended to mobilise secretions. During PEP therapy, the patient exhales against a fixed orifice resistor or a threshold resistor, generating pre-set pressures in the range of 10-20 cm H2O. These expiratory pressures may combat atelectasis by splinting open terminal airways and collapsible alveoli. The splinting of small airways also aids in mobilisation of secretions that may be trapped or plugged due to airway closure.

Several commercial devices are available for PEP therapy, known as PEP devices. These generally have a fixed orifice resistor or threshold resistor capable of developing pressures of 10-20 cm H2O. Some devices incorporate a "flutter" valve to produce oscillation during exhalation, which may further enhance secretion mobilisation. One such device is described in US2015/0053209. In one embodiment (FIGS. 1 to 6), the device includes a mouthpiece, a chamber for flow of air having an inlet and two outlets adjacent to the inlet, and a rotor configured for oscillation back and forth within the chamber. In response to the flow of air through the chamber the rotor periodically closes the air inlet. This produces an oscillation in pressure. Due to the design of the device, a large proportion of the air entering the chamber will impact on the vane on each side of its centre of rotation, thereby preventing movement of the vane from its initial position, and consequently inhibiting the generation of pressure fluctuation within the device.

US2014/041657 describes a PEP device that employs a motor or compressed air as a mechanism to effect rotation of the rotors. The inclusion of a motor adds significantly to the cost of the device as well as the regulatory challenges associated with the use of electronic devices in medical devices. The use of compressed air limits the use of the device outside of a hospital setting or a home setting.

The devices of US2015/0053209 and US2014/041657, and most commercially available PEP devices, are of relatively complex construction, and therefore expensive and intended for multiple uses. While the devices are provided with instructions on good hygiene practices for keeping the device clean and free of microbial contamination, compliance with hygiene practices is generally poor, with the result that the device becomes colonised with (opportunistic) pathogens. This often occurs despite full compliance with hygiene recommendations. These devices often therefore function as a reservoir of pathogens that does not come into contact with antimicrobial agents and which can cause re-infection. Adding to the complexity of PEP therapy is the fact that colonising bacteria may be prone to genetic adaptation and diversification into sub-populations with varying phenotypic traits and differing colony morphologies. Accordingly, there is a need for an inexpensive, single-use (disposable) PEP device.

U.S. Pat. No. 4,841,964 describes an inhalation device configured to deliver drug to a patient during inhalation through the device. The device comprises an annular chamber having an air inlet and air outlet, and a ball disposed within the annular chamber and free to rotate in response to air movement within the chamber. Drug particles are coated onto the surface of the annular chamber such that movement of the ball within the annular chamber dislodges the drug particles which are picked up in the air flow and delivered to the patient in the inhaled air. The device is not suitable for use as a PEP device, as the movement of the ball within the annular chamber does not cause cyclical fluctuations in pressure. This is because the air outlet is annular and continuous around the annular chamber—see air discharge system 7 in FIG. 1—meaning that the air is allowed to pass into the outlet continuously irrespective of the position of the ball, which results in steady air discharge during inhalation by a patient. A device configured to deliver drug with cyclical fluctuations in airflow resistance would not be desirable from the point of view of an inhaler, and was neither intended not reduced to practice with the device of U.S. Pat. No. 4,841,964.

It is an object of the invention to overcome at least one of the above-referenced problems.

STATEMENTS OF INVENTION

The present invention provides a practical and uncomplicated respiratory treatment device that in one embodiment can be assembled from three parts and provided in a miniaturised format. Due to the low manufacturing cost, it can be provided as a single-use, disposable, device that obviates the problems associated with non-compliance to hygiene practices. In a preferred embodiment, according to Claim 1, the device comprises a housing having an annular chamber, a chamber inlet configured to permit air into the annular chamber, a chamber outlet configured to permit air out of the annular chamber, and a mouthpiece in fluid communication with the chamber inlet; and a moveable body (typically a metal ball) configured to revolve around the annular chamber in response to flow of air from the chamber inlet to the chamber outlet, wherein the revolutions of the movable body around the annular chamber causes intermittent partial blocking of the chamber outlet and consequent cyclical fluctuations of airflow resistance through the device.

The device according to the invention provides an uncomplicated and easy-to-manufacture device configured to administer positive exhalation pressure (PEP) therapy to a patient by producing cyclical fluctuations of airflow resistance in response to a patient exhaling through the device. Due to the uncomplicated construction of the device, the device may be manufactured as a single-use device, which obviates the requirement of prior art devices of cleaning of the device, and also obviates the microbiological risk associated with more complicated (multi-use) devices of the prior art. The cyclical fluctuations are primarily determined by the size of the ball and annular track (and consequently the clearance between the ball and walls of the annular track), and these can be easily varied during manufacture to provide devices for a specific clinical situation, for example by varying the diameter of the track, or the clearance between the ball and the track, which can be configured to vary the frequency or rotation of the ball around the track, the average resistance to airflow and peak resistance to airflow.

In a broader aspect, the invention provides a respiratory treatment device, especially a miniature single-use PEP device, comprising:

a housing having:

a chamber, a chamber inlet configured to permit air into the chamber, a chamber outlet configured to permit air out of the chamber, and a flow path for passage of air through the chamber from the chamber inlet to the chamber outlet; and a mouthpiece in fluid communication with the chamber inlet; a rotating element disposed in the housing within the flow path and configured for rotation in response to flow of air through the chamber from the chamber inlet to the chamber outlet; wherein the rotating element is configured to close or interfere with the chamber inlet and/or chamber outlet flow causing the air flow resistance and resultant pressure to oscillate during expiration by the user.

In one embodiment of the invention, the device is miniature. In this specification, the term "miniature" as applied to a PEP device means a PEP device that has a maximum length of less than 7 cm, a maximum width of less than 4 cm, and a maximum depth of less than 2 cm.

In one embodiment of the invention, the device is single use. This means that the device is disposable and relatively inexpensive to manufacture, and the core of the device that is capable of producing cyclical fluctuations in pressure, i.e housing and rotating element, is formed from a minimum number of parts, for example three parts.

Typically, the chamber inlet and chamber outlet are disposed on substantially opposite sides of the chamber. In one embodiment, they are spaced apart, typically by at least 90° (based on the path of rotation of the rotating element). In one embodiment, they are spaced apart by at least 110°. In one embodiment, they are spaced apart by at least 130°. In one embodiment, they are spaced apart by at least 150°. In one embodiment, they are spaced apart by at least 170°.

In one preferred embodiment, the flow path is an annular track and in which the rotating element is a moveable body configured to move around the annular flow path in response to flow of air through the flow path and at least partially block the chamber inlet and/or chamber outlet intermittently during revolution around the annular flow path thereby causing cyclical fluctuations in airflow resistance. This is in contrast with the device of U.S. Pat. No. 4,841,964, where the revolutions of the ball do not intermittently at least partially close the outlet or inlet such that cyclical fluctuations in airflow resistance are generated during use.

One example of a movable body is a ball, but other rotating elements may be employed which do not necessarily have to be spherical, for example oval or disk shaped bodies. The shape of the body is not essential provided that the body can move around the annular flow path in response to flow of air and can at least partially block the chamber inlet and/or outlet as it passes thereby causing cyclical fluctuations in pressure. In one embodiment, the movable body is a weighted metal ball. In one embodiment, the moveable body is configured to block at least 75% of the area of the inlet or outlet as it passes.

In one embodiment, the air outlet is not disposed on an outer circumferential part of the annular chamber. This is because the centrifugal forces acting on the movable body (i.e. ball) can in some cases cause the ball to lodge in the outlet, which prevents correct use of the device. Thus, in preferred embodiment, the air outlet is disposed on a top, bottom or inner circumferential side (aspect) of the annular chamber.

In one embodiment, the air inlet is disposed on an outer circumferential part of the annular chamber.

In one embodiment, the movable body and air inlet are configured such that the movable body does not block the air inlet as it passes the air inlet. This is easily achieved by, for example, making the air inlet large relative to the size of the movable body.

In one embodiment, the air inlet is configured to enter the annular chamber tangentially. This arrangement ensures that the incoming air forces the movable body to move around the annular chamber in one direction.

In one embodiment, the annular track, air outlet, and movable body (i.e. size and weight of the movable body) are configured to produce a revolution rate of the movable body around the annular track of 5-50, 5-40, 5-30, 10-50, 10-40, 10-30, 20-50, 20-40 or 20-30 Hz at a flow rate of air of 10 L/minute.

In one embodiment, the annular track has a diameter (where diameter is measured from outer circumference to outer circumference) of 5-50, 10-40, 10-30, 20-50, 20-40, 25-35 mm.

In one embodiment, the movable body (i.e. ball) has a diameter (at its widest point) of 1-15, 2-10, 2-5, 5-15, 5-10 or 6-8 mm.

In one embodiment, the clearance between the movable body and the wall of the annular track is 0.1 to 1 mm.

In one embodiment, the device is a planar device. In one embodiment, the air inlet is disposed on one side of the mouthpiece.

In another embodiment of the invention, the rotating element is a rotor having at least one vane mounted within the chamber for full rotation in response to flow of air through the chamber, wherein the at least one vane is configured to at least partially block the chamber inlet and/or chamber outlet periodically during rotation of the rotor within the chamber. In one embodiment, the rotor has a plurality of vanes wherein one of the vanes is configured to at least partially block the chamber inlet and/or chamber outlet periodically during rotation of the rotor within the chamber and the other vanes are configured to not block the chamber. In one embodiment, the rotor has a plurality of vanes wherein two of the vanes are configured to at least partially block the chamber inlet and/or chamber outlet periodically during rotation of the rotor within the chamber and the other vanes are configured to not block the chamber, wherein the two closing vanes are spaced apart around the rotor.

In one embodiment, the respiratory treatment device comprises a one-way valve in the air flow path disposed upstream of the chamber. In one embodiment, the one-way valve is located within the mouthpiece. In one embodiment, the one-way valve is located within the chamber.

In one embodiment, the respiratory treatment device is configured to provide an oscillating resistance to air flow through the device, in which a peak resistance to airflow during oscillation is typically in the range of 1 to 40, 4-30, 5-30, 5-25, 10-25 or 10-20 cm $H_2O$ (typically when a flow rate of air of 10 L/minute is passed through the device). A method of measuring peak resistance to airflow and average resistance to airflow during oscillation (fluctuation) is described below.

In one embodiment, the respiratory treatment device includes a fixed-orifice resistor to airflow. In one embodiment, the fixed orifice resistor is disposed within the mouthpiece. In one embodiment, the fixed orifice resistor is disposed adjacent the chamber inlet. In one embodiment, the fixed orifice resistor is configured to provide a fixed resistance to airflow of 1-40, 4-30, 5-30, 5-25, 10-25 or 10-20 cm $H_2O$ (typically when a flow rate of air of 10 L/minute is passed through the device).

In one embodiment, the device is disposable. In one embodiment, the housing is formed from two parts which fit together to form the housing. In one embodiment, the housing is formed from a thermoplastic polymeric material. Examples of suitable thermoplastic polymeric materials include ABS, acrylic, polyurethane, polyethylene or, ideally, polycarbonate (such as Makloron™).

In one embodiment, the housing is formed from two parts which fit together to form the housing. In one embodiment, the material from which the housing is formed may have antimicrobial properties or be coated with material that has antimicrobial properties.

In one embodiment, the device consists essentially of two parts configured to fit together to form the housing and a rotating element configured to fit within the formed housing.

In one embodiment, the device comprises a counter system including a sensor configured to detect revolutions of the rotating member around the annular track operatively connected to a display configured to provide a detectable signal to the user indicative of the number of revolutions. The detectable signal may be visual, audible, tactile or another type of signal detectable by a human (for example a vibration). The detectable signal may indicate the number of revolutions, in an absolute or relative manner, the rate of revolution, or both. In one embodiment, the counter system is configured to emit a detectable signal that is indicative of a certain threshold of revolutions being completed within a predefined duration of use. In this way, the device can inform a user that a sufficient amount of therapy has been completed. Methods for detecting revolutions of the rotating member around the annular track will be well known to a person skilled in the art, and include; magnetic reed switch counter, optical based counter system, geared analog dial system or momentary non-latching switch system, amongst others.

In one embodiment, the device comprises a moisture sensor disposed in the housing within the flow path for air and configured to provide a detectable signal to the user when a reference level of moisture is detected within the housing. Examples of moisture sensors will be well known to a person skilled in the art and include sensors based on measurement of electrical resistance, dielectric constant, or interaction with neutrons, as a variable for the moisture content. Examples of moisture sensors are commercially available from the following companies: Vernier; Vegetronix; and Specmeters.

In one embodiment, the device has a maximum length (along a longitudinal aspect of the device) of less than 10 cm. In one embodiment, the device has a maximum length of less than 9 cm. In one embodiment, the device has a maximum length of less than 8 cm. In one embodiment, the device has a maximum length of less than 7 cm. In one embodiment, the device has a maximum length of less than 6 cm. In one embodiment, the device has a maximum length of less than 5 cm.

In one embodiment, the device has a maximum width (along a transverse aspect of the device) of less than 6 cm. In one embodiment, the device has a maximum width of less than 5 cm. In one embodiment, the device has a maximum width of less than 4 cm. In one embodiment, the device has a maximum width of less than 3 cm.

In one embodiment, the device has a maximum depth of less than 2 cm. In one embodiment, the device has a maximum depth of less than 1.5 cm. In one embodiment, the device has a maximum depth of less than 1.2 cm. In one embodiment, the device has a maximum depth of less than 1 cm.

In one embodiment, the device is configured to treat a respiratory disorder by means of PEP therapy. In one embodiment, the device is a PEP device. In one embodiment, the device is configured to treat atelectasis by means of PEP therapy. In one embodiment, the device is configured to effect a clinically significant mobilisation of secretions in the airway. In one embodiment, the device is configured to treat atelectasis.

In one embodiment, through single use the device avoids provision of a location/space/environment/physical space that can harbour patient-derived microorganisms.

In one embodiment, the device avoids provision of a reservoir of patient-derived microorganisms.

In another aspect, the invention provides a respiratory treatment device, especially a miniature single-use PEP device, comprising:

a housing having a chamber, a chamber inlet configured to permit air into the chamber, a chamber outlet configured to permit air out of the chamber and a mouthpiece in fluid communication with the chamber inlet, wherein the chamber defines a flow path for passage of air through the chamber from the chamber inlet to the chamber outlet;

wherein the device comprises a spring-biased closure for the chamber outlet configured to oscillate in response to airflow through the device from a first position in which the closure is spring-biased into contact with the closure to close the outlet to a second position in which the closure is spaced-apart from the outlet to open the outlet.

In one embodiment, the spring biased closure is mounted to the housing downstream of the closure. In one embodiment of the invention, the spring-biased closure comprises a blocking body configured to fit into the closure to close the closure, and a spring fixed to the housing. In one embodiment, the spring-biased closure comprises two springs each fixed to the housing. In one embodiment, the spring or each spring is a resiliently deformable U-shaped spring.

In another embodiment, the invention provides a kit of parts comprising a device of the invention and a plurality of movable bodies of characteristics (i.e different size or weight), whereby the housing is configured to be opened by a user to enable a user insert a movable body of their choice. This provides for a kit configured to treat different clinical situations, whereby a patient can choose the required parameters of operation of the device (i.e. peak resistance to airflow, frequency of cyclical fluctuations) by choosing a movable body configured to provide the required parameters.

The invention also relates to a method for treatment of a respiratory disorder which employs a respiratory treatment device (or kit) of the invention, the method comprising the steps of placing the mouthpiece in the mouth of a patient, and the patient exhaling through the mouthpiece, wherein the device produces an oscillating resistance to exhalation airflow.

The invention also relates to a method for administering respiratory physiotherapy to a patient which employs a respiratory treatment device (or kit) of the invention, the method comprising the steps of placing the mouthpiece in the mouth of a patient, and the patient exhaling through the mouthpiece, wherein the device produces an oscillating resistance to exhalation airflow.

The invention also relates to a device (or kit) of the invention for use in treatment of a respiratory disorder.

The invention also relates to a device (or kit) of the invention for use in administering respiratory physiotherapy to a patient.

In one embodiment, the respiratory disorder is selected from atelectasis, cystic fibrosis, asthma, bronchitis, bronchial asthma, bronchiectasis and primary ciliary dyskinesia syndrome.

BRIEF DESCRIPTION OF THE FIGURES

The invention will be more clearly understood from the following description of some embodiment thereof, given by way of example only, with reference to the accompanying figures in which:

FIGS. 1A to 1C are front elevational, side elevational, and top plan, views of a respiratory treatment device according to one embodiment of the invention;

FIGS. 8A to 8C are front elevational, side elevational, and top plan, views of a respiratory treatment device according to a second embodiment of the invention;

FIG. 9 is an exploded perspective view of the device of FIG. 8 showing the rotor;

FIGS. 22A to 22C are front elevational, side elevational, and top plan, views of a respiratory treatment device according to a fourth embodiment of the invention;

FIG. 23 is an exploded perspective view of the device of FIG. 22 showing the rotor;

DETAILED DESCRIPTION OF THE INVENTION

Figure 2:
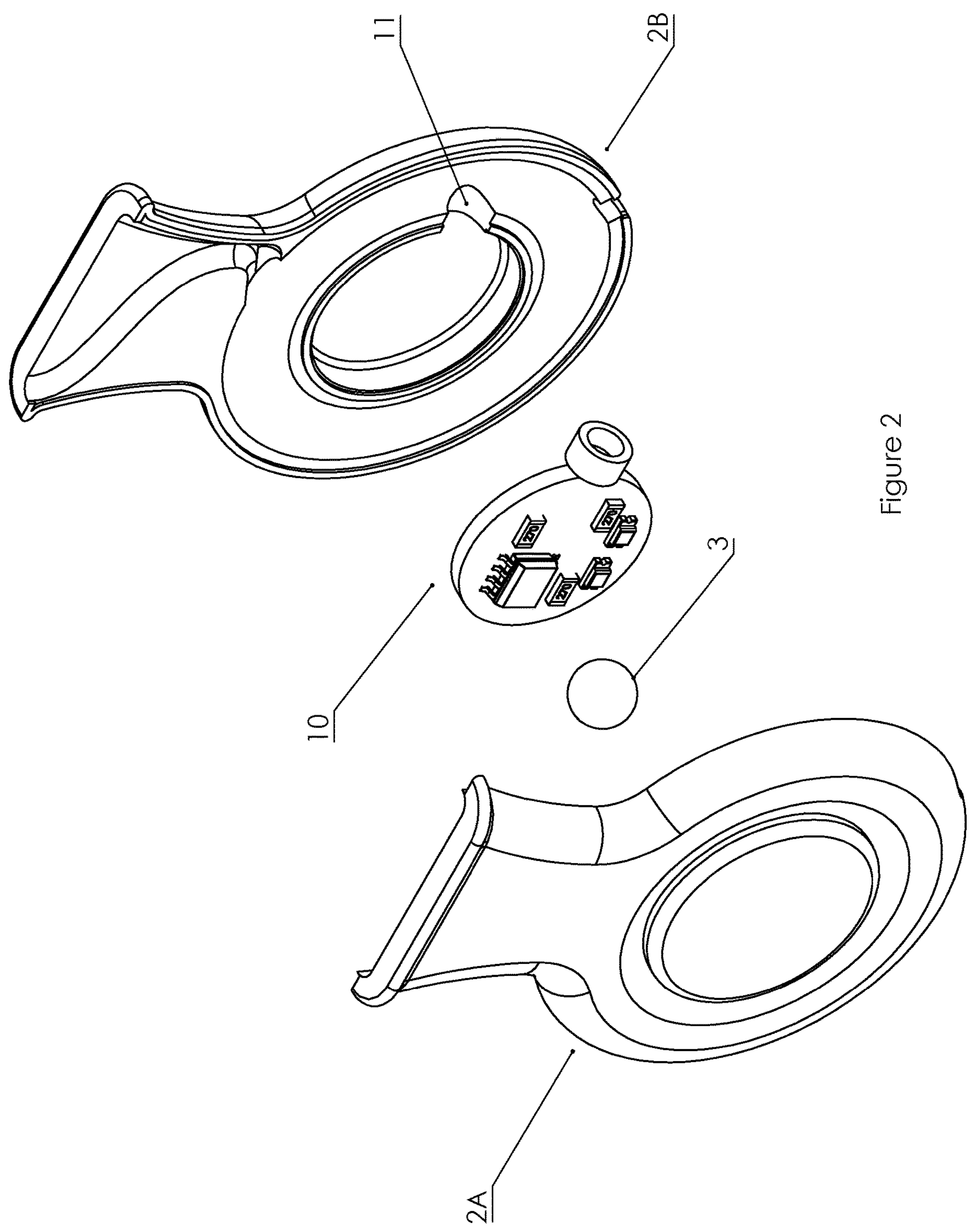
FIG. 2 is an exploded perspective view of the device of FIG. 1 including an additional PCB component.

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions and General Preferences:

Where used herein and unless specifically indicated otherwise, the following terms are intended to have the following meanings in addition to any broader (or narrower) meanings the terms might enjoy in the art: Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, poisoning or nutritional deficiencies.

As used herein, the term "treatment" or "treating" refers to an intervention (e.g. the administration of an agent to a subject) which cures, ameliorates or lessens the symptoms of a disease or removes (or lessens the impact of) its cause(s). In this case, the term is used synonymously with the term "therapy".

Additionally, the terms "treatment" or "treating" refers to an intervention (e.g. the administration of an agent to a subject) which prevents or delays the onset or progression of a disease or reduces (or eradicates) its incidence within a treated population. In this case, the term treatment is used synonymously with the term "prophylaxis".

As used herein, an effective amount or a therapeutically effective amount of an agent defines an amount that can be administered to a subject without excessive toxicity, irritation, allergic response, or other problem or complication, commensurate with a reasonable benefit/risk ratio, but one that is sufficient to provide the desired effect, e.g. the treatment or prophylaxis manifested by a permanent or temporary improvement in the subject's condition. The amount will vary from subject to subject, depending on the age and general condition of the individual, mode of administration and other factors. Thus, while it is not possible to specify an exact effective amount, those skilled in the art will be able to determine an appropriate "effective" amount in any individual case using routine experimentation and background general knowledge. A therapeutic result in this context includes eradication or lessening of symptoms, reduced pain or discomfort, prolonged survival, improved mobility and other markers of clinical improvement. A therapeutic result need not be a complete cure.

In the context of treatment and effective amounts as defined above, the term subject (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; and ungulates such as deer and giraffes. In preferred embodiments, the subject is a human.

"Peak resistance to airflow" refers to the average of the highest resistance to airflow measured in a device of the invention during cyclical fluctuations in airflow resistance. It is measured as the air pressure at the mouthpiece in $mmH_2O$. The mechanical behaviour of the device of the invention can be tested experimentally under lab conditions. A compressed air supply is attached via a needle valve to a mass air flow meter (Honeywell, AWM720P1). The mass flow meter is connected to Labview, via a 14-bit resolution USB Data acquisition card (USB-6001, National Instruments). A high precision pressure transducer (Freescale MPX5050) is also connected to the data acquisition card to record average and peak resistance values. Values for flow were recorded in Liters per Minute (LPM) with pressure measured in Millimeters of Water (mmH2O). Data from Labview were exported to Excel for further analysis.

In this specification, the term "respiratory disorder" should be understood to mean a disease or disorder characterised by excessive mucus production in the pulmonary airways (i.e. cystic fibrosis), or defective ciliary function (primary ciliary dyskinesia syndrome), respiratory dysfunction, obstructive lung disease (chronic bronchitis, chronic obstructive pulmonary disease (COPD), emphysema) or reduced pulmonary function (atelectasis, pneumothorax, bronchial asthma).

Exemplification

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Referring to the drawings, and initially to FIGS. 1 to 7, there is illustrated a respiratory treatment device according to a first embodiment of the invention and indicated generally by the reference numeral 1. The device comprises a housing 2 and a movable body, in this case a weighted ball 3, disposed within the housing 2. The housing is provided in two parts 2A and 2B which fit together to form an annular ring-shaped chamber 5, having a chamber inlet 6 and a chamber outlet 7 circumferentially spaced apart at an angle of about 150 degrees, and a mouthpiece 8 in fluid communication with the chamber inlet 6. The weighted ball 3 is dimensioned to fit within the chamber in an airtight manner while allowing the ball revolve around the annular chamber.

In use, when a user exhales into the device the airflow forces the ball to revolve around the annular chamber in a cyclical manner. The ball is dimensioned to partially block the chamber inlet 6 and outlet 7 periodically as it revolves around the annular chamber causing an oscillating resistance to airflow, which enhances mobilisation of pulmonary secretions.

The mouthpiece 8 takes the shape of a substantially flat funnel, tapering inwardly towards the chamber inlet 6. A fixed resistance orifice 9 is formed at a distal end of the mouthpiece 8 just proximal of the chamber inlet 6.

Figures 3, 4, 5, 6, 7:
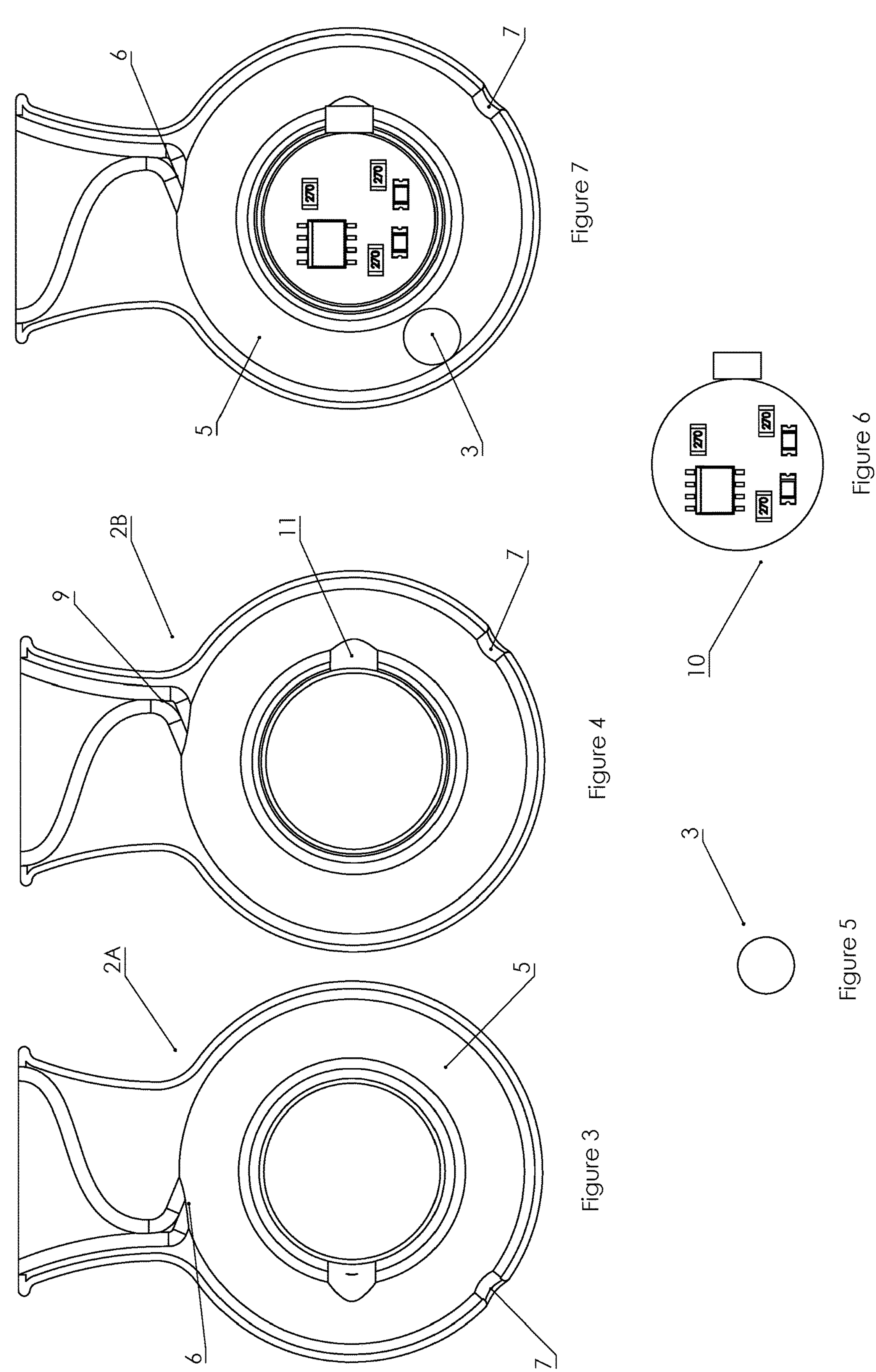
FIGS. 3 and 4 are front elevational views of the two-parts of the housing forming part of the device of FIG. 1.
FIG. 5 illustrates a ball that represents one embodiment of the movable body part of the device of FIG. 1.
FIG. 6 illustrates a PCB board that forms part of a device according to one embodiment of the invention.
FIG. 7 is a front elevational view of one part of the housing shown in FIG. 4 that makes up the device of FIG. 1, showing the PCB board in-situ.

A PCB board 10 configured to measure the number of revolutions of the ball around the annular chamber 5 is shown in FIG. 6, and show in-situ in the device in FIG. 7. The PCB board 10 is dimensioned to snap-fit into the recess defined by an inner circumference of the annular chamber 5, with an inner part of the annular chamber having an opening 11 to allow sensors on the PCB board 10 access to the annular chamber. The PCB may also include an electrical moisture sensor which can be employed to measure moisture as an indicator of when the device has reached the end of its usable life. The PCB typically also comprises a display, visible to the user, for providing data concerning the number of revolutions of the weighted ball or rotor and/or an indication of when the device has reached the end of its usable life.

In use, the mouthpiece of the device is placed in a users' mouth and the user exhales through the mouthpiece forcing air though the fixed resistance orifice 9 and into the chamber 5 through the chamber inlet 6 where the moving air under pressure forces the ball 3 to revolve around the annular chamber. The fixed resistance orifice 9 provides a resistance to flow that is sufficient to help splint open terminal airways in the users' lungs and helps mobilise secretions that may be trapped or plugged due to airway closure. As the ball revolves around the annular chamber, it periodically partially obstructs the chamber inlet 6 and chamber outlet 7 which causes the resistance to flow to increase dramatically on two occasions during each revolution of the ball causing an oscillating resistance to airflow, which enhances mobilisation of pulmonary secretions.

Figures 10, 11, 12, 13, 14:
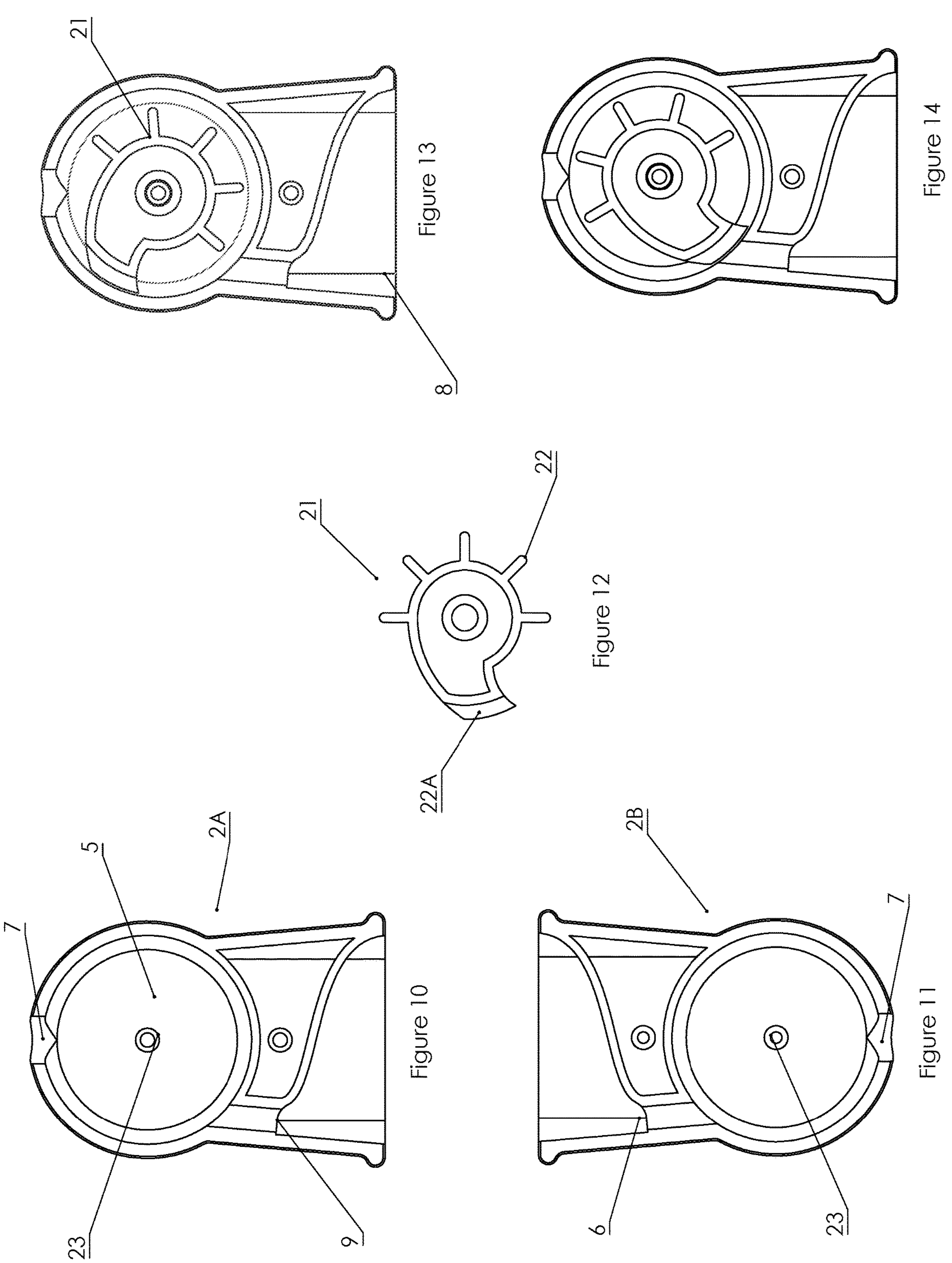
FIGS. 10 and 11 are front elevational views of the two-parts of the housing forming part of the device of FIG. 8.
FIG. 12 illustrates a rotor forming part of the device of FIG. 8.
FIGS. 13 and 14 are front elevational views of one part of the housing showing the rotor in different positions.
Figures 15A, 15B, 15C, 16:
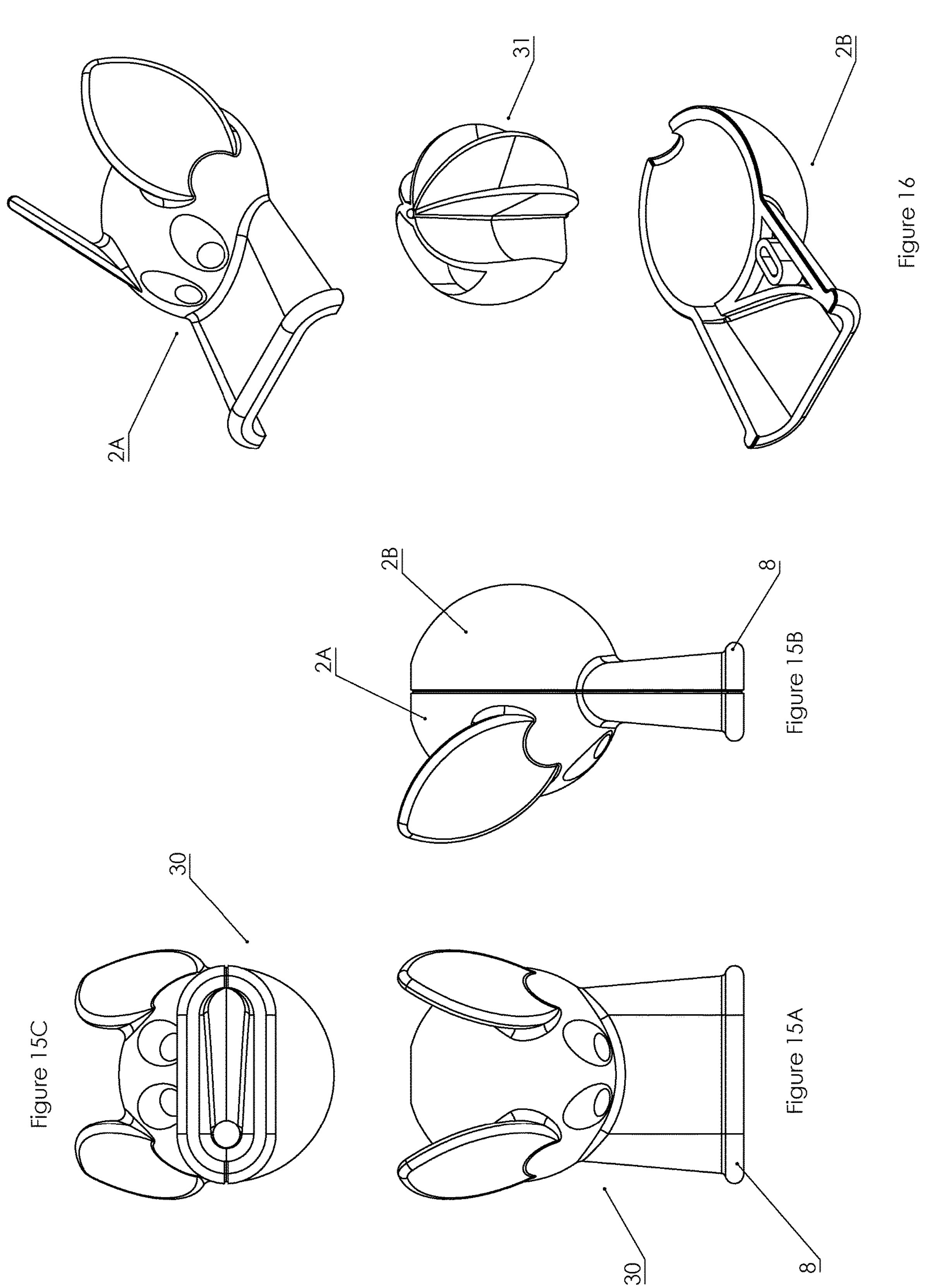
FIGS. 15A to 15C are front elevational, side elevational, and top plan, views of a respiratory treatment device according to a third embodiment of the invention.
FIG. 16 is an exploded perspective view of the device of FIG. 15 showing the rotor.
Figures 17, 18, 19, 20, 21:
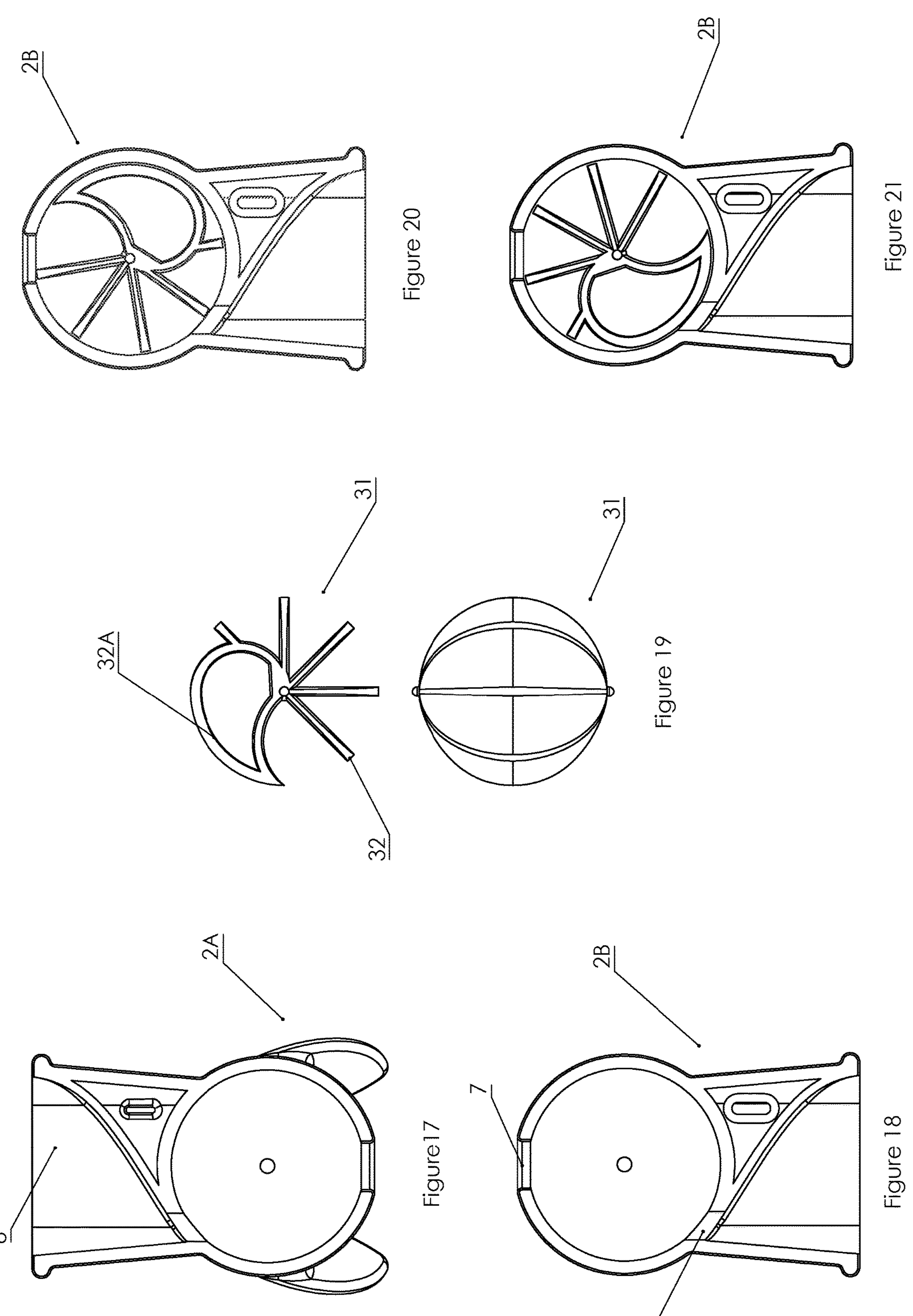
FIGS. 17 and 18 are front elevational views of the two-parts of the housing forming part of the device of FIG. 15.
FIG. 19 illustrates a rotor forming part of the device of FIG. 15.
FIGS. 20 and 21 are front elevational views of one part of the housing showing the rotor is two different positions.
Figures 24, 25, 26, 27:
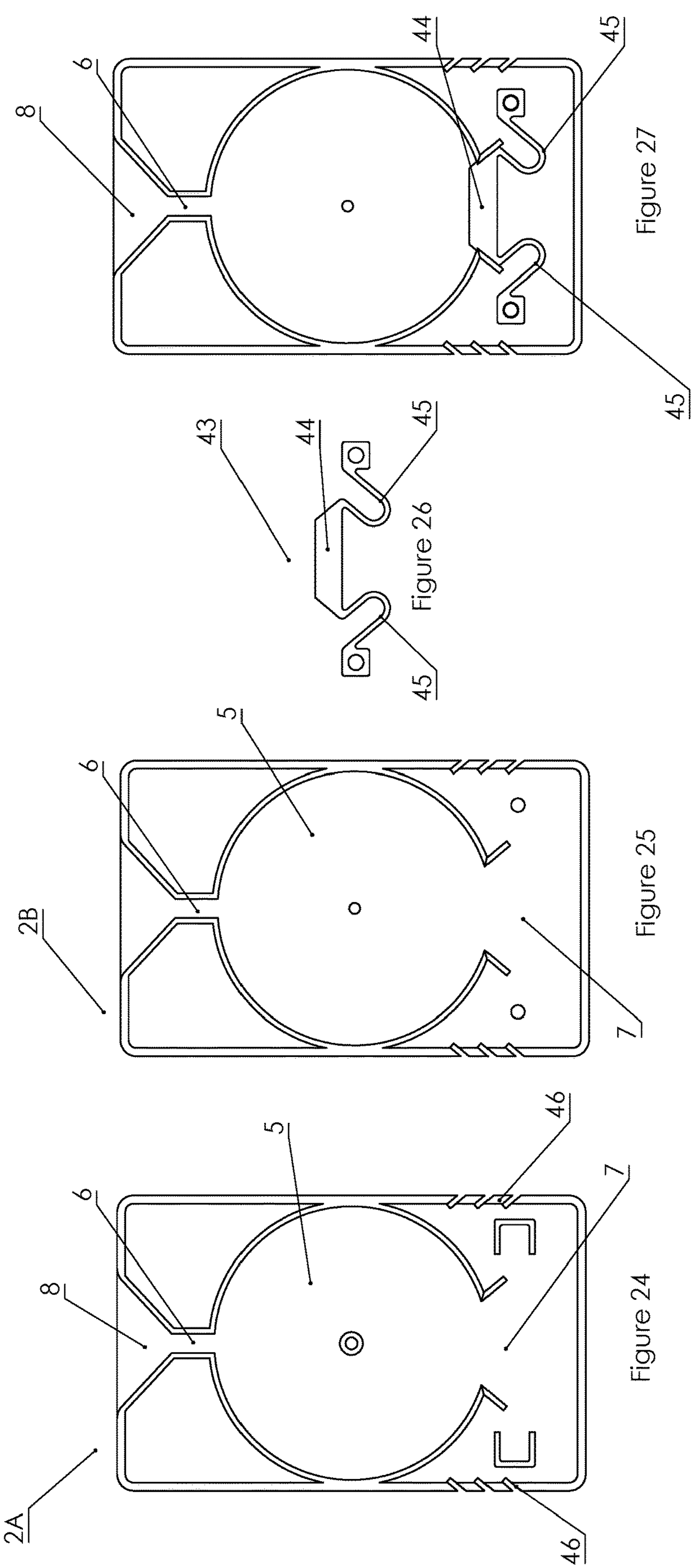
FIGS. 24 and 25 are front elevational views of the two-parts of the housing forming part of the device of FIG. 22.
FIG. 26 Illustrates a spring-biased closure forming part of the device of FIG. 22.
FIG. 27 is a front elevational view of one part of the housing shown in FIG. 22 and having the spring biased closure in-situ.

Referring now to FIGS. 8 to 14, an alternative embodiment of the device of the invention is described, indicated generally by the reference numeral 20, in which parts identified with reference to FIGS. 1 to 7 are assigned the same reference numerals. In this embodiment, oscillating resistance to airflow through the device is provided by a rotating rotor as opposed to a revolving ball. Thus, in this embodiment, the chamber 5 has a generally cylindrical shape and a cylindrical rotor 21 is mounted to the housing for rotation within the cylindrical chamber 5. The rotor 21 has six vanes 22, including a blocking vane 22A that is configured to periodically partially block the chamber outlet 7 during rotation (as shown in FIG. 14). As shown in FIGS. 10 and 11, each of the two parts of the housing 2A, 2B have mounts 23 for rotatable mounting of the rotor 21 within the housing. The rotor 21 is dimensioned to fit snugly within the chamber in a substantially airtight manner to ensure that air can only pass through the chamber from the inlet to the outlet when the rotor rotates. The use of this embodiment of the invention is the same as that described with reference to the previous embodiment.

Referring to FIGS. 15 to 21, there is illustrated an alternative embodiment of a respiratory treatment device of the invention in which parts described with reference to the previous embodiment have been assigned the same reference numerals. In this embodiment, the device indicated generally with the reference numeral 30 has a round chamber 5 and a round rotor 31 dimensioned to fit within the chamber. The vanes 32 are semi-circular, and the blocking vane 32A is formed by a circumferential band connecting two or more adjacent vanes. The top part of the housing also includes ear formations and eye graphics to make the device resemble a head of an animal, which makes the device more user-friendly for a child user. The use of this device is substantially the same as that described with reference to the device of FIGS. 8 to 14.

In the embodiments shown, the device has a maximum length of 4.5 cm, a maximum width of about 2 cm, and a maximum depth of about 1.2 cm. Compared with the prior art devices, it is therefore a miniaturised device which has only three parts including only one moving part, and is therefore simple and relatively inexpensive to produce.

Referring to FIGS. 22 to 27, an alternative embodiment of the device of the invention is described, indicated generally by the reference numeral 40, in which parts described with reference to the previous embodiments are assigned the same reference numerals. In this embodiment, the device has a credit card shape, and is formed from three parts namely two parts of the housing 42A and 42B, and a spring-biased closure 43. In more detail, the closure 43 comprises a wedge-shaped body 44 configured to fit snugly within the chamber outlet 7 and two U-shaped mounts 45 fixed at one end to the housing and an opposite end to the body 44 such that when a force is applied to the body 44 deformation of the U-shaped mounts allow movement of the body 44 away from the closure to open the closure. Air exiting the chamber 5 through the outlet 7 exist the housing through vents 46 formed on each side of the distal end of the housing. In use, when the user exhales into the mouthpiece 8 through the fixed orifice resistor 6, air pressure increases in the chamber 5.

Once the pressure in the chamber 5 has exceeds the closing pressure of the spring biased closure 23, the U-shaped mounts 45 deform, moving the wedge shaped body 44 out of contact with the chamber outlet 7 and permitting air to escape via the vents 46 on either side of the housing. The resultant drop in pressure in the chamber 5 allows the spring biased closure 23 to return to the closed position with the wedge-shaped body 44 fitting snugly into the chamber outlet 7. This action repeats to provide oscillation of the air pressure.

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. A device, comprising:

a housing including a chamber defining an annular track having an inner diameter and an outer diameter, an inlet disposed on an outer circumferential aspect of the annular track and configured to permit air into the chamber, an outlet configured to permit air out of the chamber, and a mouthpiece in fluid communication with the inlet, wherein the housing defines a flow path including, in order from an upstream end of the flow path to a downstream end of the flow path, the mouthpiece, the inlet, the annular track, and the outlet; and a body disposed within the chamber such that the body is configured to revolve around the annular track defined by the chamber, wherein the body is configured to cause cyclical fluctuations of airflow resistance through the device by at least partially interfering with the inlet or the outlet during revolutions around the annular track.

2. The device of claim 1, wherein the body is configured to fit within the chamber in a substantially airtight manner.

3. The device of claim 1, wherein the body is a weighted ball.

4. The device of claim 1, wherein the mouthpiece tapers inwardly toward an orifice formed at a distal end of the mouthpiece proximal of the inlet.

5. The device of claim 4, wherein the orifice is a fixed resistance orifice.

6. The device of claim 1, wherein the outlet is disposed on an inner circumferential aspect of the annular track defined by the chamber.

7. The device of claim 1, wherein the housing is comprised essentially of two parts that fit together to form the chamber.

8. The device of claim 1, wherein the body is configured to revolve around the annular track defined by the chamber in response to flow of air through the chamber.

9. The device of claim 1, wherein the inlet and the outlet are circumferentially spaced apart by at least 90° around the annular track.

10. The device of claim 1, wherein the body is configured to block at least 75% of an area of the inlet or the outlet as it passes.

11. A device, comprising:

a housing including a chamber defining annular track having an inner diameter and an outer diameter sharing a first central axis, an inlet disposed on an outer circumferential aspect of the annular track and configured to permit air into the chamber, an outlet disposed on a top, bottom, or inner circumferential aspect of the annular track defined by the chamber and configured to permit air out of the chamber, and a mouthpiece in fluid communication with the inlet, wherein the housing defines a flow path including, in order from an upstream end of the flow path to a downstream end of the flow path, the mouthpiece, the inlet, the annular track, and the outlet; and a body including a second central axis and disposed within the chamber such that the body is free to revolve around the first central axis of the annular track and rotate about the second central axis of the body, wherein the body is configured to cause cyclical fluctuations of airflow resistance through the device by at least partially interfering with the inlet or the outlet during revolutions around the annular track.

12. The device of claim 11, wherein a clearance between the body and a wall of the annular track is between 0.1 mm and 1 mm.

13. The device of claim 11, wherein the mouthpiece is shaped in the form of a substantially flat funnel.

14. The device of claim 13, wherein the mouthpiece tapers inwardly toward the inlet.

15. The device of claim 11, wherein the housing is comprised essentially of two parts that fit together to form the chamber.

16. A device, comprising:

a housing including a chamber defining an annular track, an inlet disposed on an outer circumferential aspect of the annular track and configured to permit air into the chamber, an outlet configured to permit air out of the chamber, and a mouthpiece in fluid communication with the inlet, wherein the housing defines a flow path including, in order from an upstream end of the flow path to a downstream end of the flow path, the mouthpiece, the inlet, the annular track, and the outlet; and a ball disposed within the chamber and configured to cause cyclical fluctuations of airflow resistance by at least partially interfering with the inlet or the outlet during revolutions around the annular track.

17. The device of claim 16, wherein the ball is a metal ball.

18. The device of claim 16, wherein the ball has a diameter between 5 cm and 10 cm.

19. The device of claim 16, wherein the ball is configured to block at least 75% of an area of the inlet as the ball passes the inlet.

20. The device of claim 16, wherein the ball is configured to block at least 75% of an area of the outlet as the ball passes the outlet.

* * * * *